(12) United States Patent
Kazen et al.

(10) Patent No.: US 6,991,457 B2
(45) Date of Patent: Jan. 31, 2006

(54) ENDODONTIC OBTURATOR WITH DISPOSABLE CARTRIDGE

(75) Inventors: Glenn D. Kazen, Snohomish, WA (US); Jan Wietecha, Bothell, WA (US)

(73) Assignee: Aseptico, Inc., Woodinville, WA (US)

( * ) Notice: Subject to any disclaimer, the term of this patent is extended or adjusted under 35 U.S.C. 154(b) by 43 days.

(21) Appl. No.: 10/431,296

(22) Filed: May 6, 2003

(65) Prior Publication Data

US 2004/0224282 A1 Nov. 11, 2004

(51) Int. Cl.
*A61C 3/00* (2006.01)
*A61C 5/04* (2006.01)

(52) U.S. Cl. .......................................... 433/32; 433/90

(58) Field of Classification Search ................. 433/32, 433/81, 90, 89, 102, 224
See application file for complete search history.

(56) References Cited

U.S. PATENT DOCUMENTS

| | | | |
|---|---|---|---|
| 4,265,618 A | | 5/1981 | Herskovitz et al. |
| 4,357,136 A | | 11/1982 | Herskovitz et al. |
| 4,582,488 A | | 4/1986 | Newman |
| 4,684,334 A | | 8/1987 | Brockway |
| 5,336,088 A | * | 8/1994 | Discko, Jr. ................... 433/90 |
| 6,312,254 B1 | * | 11/2001 | Friedman ...................... 433/32 |
| 6,416,320 B1 | * | 7/2002 | Roffe et al. ................... 433/32 |
| 6,503,084 B2 | * | 1/2003 | Evers et al. ................ 433/226 |
| 6,524,102 B2 | * | 2/2003 | Davis .......................... 433/32 |
| 6,616,448 B2 | | 9/2003 | Friedman |
| 2002/0086264 A1 | * | 7/2002 | Okawa et al. ................ 433/89 |

FOREIGN PATENT DOCUMENTS

EP 0522239 A 1/1993

* cited by examiner

*Primary Examiner*—Cary E. O'Connor
(74) *Attorney, Agent, or Firm*—Graybeal Jackson Haley LLP

(57) ABSTRACT

An endodontic obturator includes a body and a disposable cartridge containing gutta percha that is couplable with the body. By containing the gutta percha in a disposable cartridge, a dentist or other medical technician does not have to clean the body or other components of the obturator, thus reducing the amount of time required to clean the obturator after use. The obturator also includes a heater operable to heat the gutta percha in the disposable cartridge and a thermal barrier operable to resist the flow of heat from the heater to the rest of the body. In addition, the obturator includes a mechanism operable to generate pressure in the disposable cartridge to dispense the gutta percha. With the thermal barrier, a portion of the obturator's body that a dentist or other medical technician might hold while injecting gutta percha into a patient's tooth may be kept relatively cool.

20 Claims, 3 Drawing Sheets

ENDODONTIC OBTURATOR WITH DISPOSABLE CARTRIDGE

BACKGROUND

Dentists or other medical technicians often remove the dental pulp from a patient's tooth when the pulp is infected or decayed to preserve the health of the patient's tooth and/or jaw. After removing the tooth's pulp, the dentist or other medical technician typically obturates the tooth, i.e., fills and seals the hollow chamber in the tooth created by the removal of the pulp to prevent food and germs from causing an infection in the tooth and/or jaw. The dentist or other medical technician typically obturates the tooth by injecting gutta percha—a plastic material that becomes soft and malleable when heated but becomes hard without being brittle when cooled—or other suitable material into the tooth's hollow chamber. Once the hollow chamber is filled, the dentist or other medical technician seals the chamber to complete the procedure.

The dentist or other medical technician typically uses an endodontic obturator or endodontic syringe to inject gutta percha or other suitable material into a tooth. FIG. 1 shows a conventional endodontic obturator 10 that a dentist or other medical technician typically uses. The obturator 10 includes a body 12 having a chamber 14 that a dentist or other medical technician places gutta percha or other suitable material in. The obturator 10 also includes a hollow cannula 16, a heater 18 to heat the gutta percha placed in the chamber 14 and thus soften the gutta percha, and a rod 20 to force the gutta percha through the cannula 16. To inject gutta percha into a tooth with the obturator 10, the dentist or other medical technician first places gutta percha into the chamber 14. Then, the dentist or other medical technician heats the gutta percha with the heater 18. Once the gutta percha is soft enough to flow through the cannula 16, the dentist or other medical technician places the cannula 18 at or inside the hollow chamber in the tooth and forces the rod 20 against the gutta percha.

Unfortunately there are some problems with using the endodontic obturator 10. If the dentist or other medical technician is not careful when using the obturator 10, he/she could burn himself/herself and/or the patient. The temperature the gutta perch must reach before it can flow through the cannula 16 is typically 65° C. Thus, the heater has to generate a substantial amount of heat that may heat other regions of the body 12, such as a region that lies in close proximity to the patient's lips or tongue or a region where the dentist or other medical technician holds the obturator 10. Consequently, the dentist or other medical technician could burn the patient if he/she inadvertently contacts the patient's mouth, or drops the obturator 10 due to the heat.

In addition, the chamber 14 and cannula 16 has to be cleaned after each procedure. To clean the obturator 10, the obturator 10 must be disassembled, and the chamber 14 and cannula 16 soaked in chloroform to dissolve the remaining gutta percha. The disassembly of the obturator 10 is time consuming, and thus an inefficient use of the dentist's or other medical technician's time. Because chloroform is very dangerous to a person's health, safety procedures must be strictly observed when handling and working with chloroform. Following the safety procedures can be time consuming, and thus an inefficient use of the dentist's or other medical technician's time. Furthermore, following the safety procedures does not ensure that an accident will not occur while handling and/or working with the chloroform.

Thus, there is a need for an endodontic obturator that may be used safely and subsequently cleaned quickly and safely.

SUMMARY

In one aspect of the invention, an endodontic obturator includes a body and a disposable cartridge containing gutta percha that is couplable with the body. The endodontic obturator also includes a heater operable to heat the gutta percha in the disposable cartridge and a thermal barrier operable to resist the flow of heat from the heater to the rest of the body. In addition, the endodontic obturator includes a mechanism operable to generate pressure in the disposable cartridge to dispense the gutta percha from the cartridge. With the thermal barrier, a portion of the obturator's body that a dentist or other medical technician might hold while injecting gutta percha into a patient's tooth may be kept relatively cool.

To dispense gutta percha from the obturator, a dentist or other medical technician couples a disposable cartridge containing the gutta percha with the body of the obturator. Then he/she heats the gutta percha to a temperature at which the gutta percha more easily flows. Then he/she generates pressure in the disposable cartridge by moving a ram of the mechanism toward the disposable cartridge. When he/she is finished dispensing the gutta percha from the obturator, he/she removes the disposable cartridge from the body and may throw it away. By containing the gutta percha in a cartridge that is disposed of after use, a dentist or other medical technician does not have to clean the body or other components of the obturator with chloroform. Furthermore, the amount of time required to clean the obturator after use is significantly reduced.

In another aspect of the invention, a disposable cartridge includes a housing defining a chamber operable to hold gutta percha, and a cannula coupled with the housing and operable to dispense the gutta percha from the housing. The housing includes a first aperture operable to receive a ram for generating pressure inside the chamber, and a second aperture operable to allow the gutta percha to flow out of the chamber. The cannula may be fixed to the housing of the disposable cartridge. Or the cannula may be removable and replaceable so that a dentist or other medical technician may use a variety of cannulas having different forms as desired. For example one cannula may be substantially straight and another cannula may be bent 90° or any other desired angle.

DETAILED DESCRIPTION

In the following detailed description of exemplary embodiments of the invention, reference is made to the accompanying drawings, which form a part hereof. The detailed description and the drawings illustrate specific exemplary embodiments by which the invention may be practiced. These embodiments are described in sufficient detail to enable those skilled in the art to practice the invention. It is understood that other embodiments may be utilized, and other changes may be made, without departing from the spirit or scope of the present invention. The following detailed description is therefore not to be taken in a limiting sense, and the scope of the present invention is defined only by the appended claims.

Figure 1:
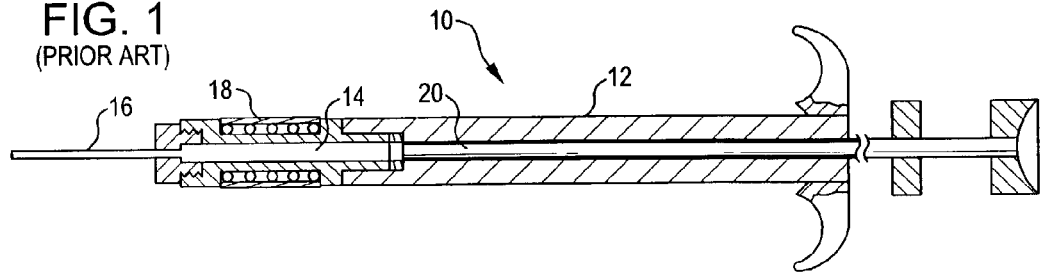
FIG. 1 is a cross-sectional view of a conventional endodontic obturator.
Figure 2:
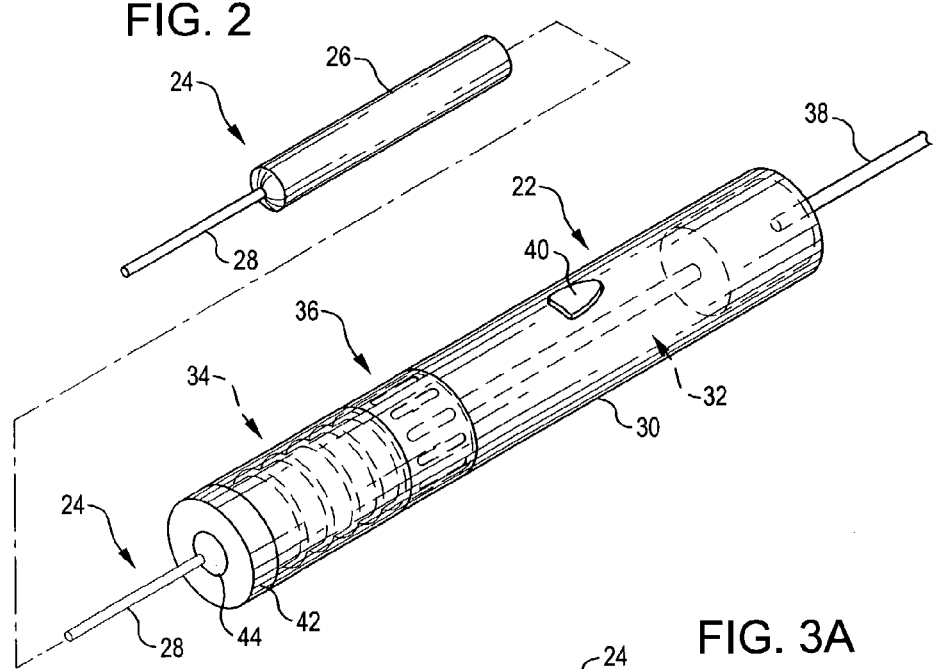
FIG. 2 is a perspective view of an endodontic obturator that includes a disposable cartridge according to an embodiment of the invention.

FIG. 2 is a perspective view of an endodontic obturator 22, according to an embodiment of the invention, that may be used by a dentist or other medical technician to inject gutta percha or other malleable material into a patient's tooth. Although this specification discusses dispensing gutta percha with the invention, the invention may dispense other malleable materials. The obturator 22 includes a disposable cartridge 24 having a housing 26 to contain gutta percha (not shown) and a hollow cannula 28 to dispense the gutta percha from the housing 26. The endodontic obturator 22 also includes a body 30 with which the disposable cartridge 24 is coupled, and a mechanism 32 to generate pressure inside the housing 26 to dispense the gutta percha from the cartridge 24. In addition, the obturator 22 includes a heater 34 to raise the temperature of the gutta percha in the cartridge 24 to soften and help dispense the gutta percha, and a thermal barrier 36 to resist the flow of heat from the heater 34 toward other components and regions of the obturator 22. The cable 38 supplies power, which may be electricity, to the mechanism 32 and heater 34, and the switch 40 allows the dentist or other medical technician to turn the mechanism 32 and heater 34 on and off.

The cartridge 24 may be coupled with the body 30 of the obturator 22 using any desired fastening technique that secures the cartridge 24 with the body 30 while a dentist or other medical technician dispenses gutta percha from the cartridge 24, and that allows the dentist or other medical technician to quickly and easily couple/remove the cartridge 24 with/from the obturator 22 when desired. For example, in one embodiment, the cartridge 24 may be inserted into a cartridge receptacle (not shown but discussed in greater detail in conjunction with FIG. 4) of the body 30 and may be secured to the obturator with an attachment element 42. As discussed in greater detail in conjunction with FIG. 4, the attachment element 42 may be threadingly coupled with the body 30 and have an aperture 44 through which the cannula 28 protrudes when the cartridge 24 is coupled with the body 30.

Other fastening techniques are contemplated. For example, a conventional locking cam mechanism may couple the cartridge 24 with the obturator 22. In such a locking cam mechanism, the attachment element 42 or the cartridge 24 may include a tongue that may be inserted into a groove of the body 30 to secure the cartridge 24 to the body 30. Or the cartridge 24 may be coupled with the obturator 22 by inserting the cartridge 24 into a slot in the obturator 22 like a tube of caulk inserted into a caulking gun. Or, the cartridge 24 may be coupled with the obturator 22 with a conventional quick-connect/disconnect mechanism like that found with many pneumatic tools for coupling the tool to a compressed gas distribution line. Or, the cartridge 24 may include threads that can engage corresponding threads in the body 30 to couple the cartridge 24 with the obturator 22.

To dispense gutta percha from the cartridge 24, the dentist or other medical technician first couples the disposable cartridge 24 containing the gutta percha with the body 30 of the obturator 22. Then, with the heater 34, he/she heats the gutta percha to a temperature at which the gutta percha more easily flows—typically around 65° C. Then, with the mechanism 32, he/she generates pressure inside the housing 26 of the cartridge 24 (as discussed in greater detail in conjunction with FIG. 5) that causes the gutta percha to flow through the cannula 28. When he/she is finished dispensing the gutta percha from the obturator 22, he/she removes the disposable cartridge 24 from the body 30 and may throw the cartridge 24 away. By containing the gutta percha in a cartridge 24 that is disposed of after use, a dentist or other medical technician does not have to clean the body 30 or other components of the obturator 22 with chloroform. Furthermore, the amount of time required to clean the obturator 22 is significantly reduced.

Figure 3A:
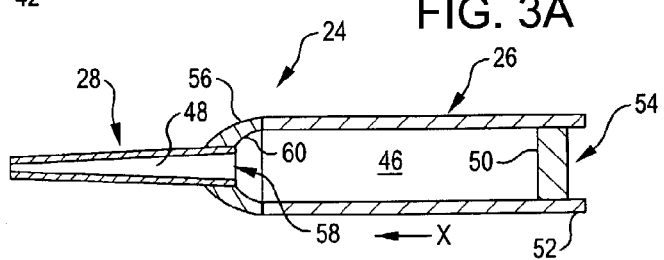
FIG. 3A is a cross-sectional view of the disposable cartridge in FIG. 2 according to an embodiment of the invention.

FIG. 3A is a cross-sectional view of the disposable cartridge 24 in FIG. 2 according to an embodiment of the invention. The cartridge 24 includes a housing 26 defining a chamber 46 having a volume in which gutta percha is disposed, and a cannula 28 having a conduit 48 through which the gutta percha may flow when the gutta percha is dispensed from the cartridge 24. To dispense the gutta percha from the cartridge 24, pressure is first generated inside the chamber 46. Once a sufficient amount of pressure is generated inside the chamber 46 (which mostly depends on the temperature of the gutta percha), the gutta percha will begin to flow through the conduit 48.

The pressure in the chamber 46 may be generated using any desired technique, such as reducing the volume of the chamber 46. In one embodiment, the housing 26 may include a wall 50 that may be moved in the X direction to reduce the volume of the chamber 46, and thus compress the gutta percha in the chamber 46. As discussed in greater detail in conjunction with FIG. 5, the wall 50 may be moved in the X direction by a component (not shown) of the mechanism 32 (FIG. 2). To allow the component to move the wall 50, the housing 26 may include a first end 52 having a first aperture 54 through which the component may pass to contact the wall 50. The housing 26 may also include a second end 56 having a second aperture 58 in fluid communication with the conduit 48. When the gutta percha in the chamber 46 is sufficiently compressed, the gutta percha will begin to flow through the second aperture 58 and the conduit 48 of the cannula 28.

Other methods of generating pressure inside the housing 26 are contemplated. For example, air may be injected into the chamber 46 through an aperture in the housing 26. Or the temperature inside the chamber 46 may be elevated to expand air and/or gutta perch in the chamber, and thus increase the pressure in the housing 26.

The cannula 28 may be fixed to the housing 26 using any desired fastening technique. For example, in one embodiment, the cannula 28 may be brazed to the second end 56, which may include an interior surface 60 configured to funnel the gutta percha into the conduit 48 of the cannula 28. This may be desirable to minimize the amount of gutta percha remaining in the cartridge when the cartridge is disposed of.

The cannula 28 and housing 26 may be made of any desirable material capable of withstanding temperatures sufficient to soften the gutta percha contained in the chamber 46, and the pressures sufficient to dispense the gutta percha from the cartridge 24. Furthermore the cannula 28 and housing 26 may have any desired shape, and the chamber 26 of the housing may have any desired volume. For example, in one embodiment, the housing 26 and cannula 28 may be made from silver, which typically does not stain or discolor gutta percha. The housing 26 may be cylindrical to correspond with the shape of the cartridge receptacle (discussed in greater detail in conjunction with FIG. 4) of the body 30 (FIG. 2), and the cannula 28 may be substantially straight. Furthermore, the volume of the chamber 46 may be 105 mm$^3$. In other embodiments, the cannula 28 may be curved to facilitate injecting gutta percha into a patient's tooth that may be located in the back of the patient's mouth. In still other embodiments, the cannula 28 and housing 26 may be made of any conventional metal, such as steel or aluminum. To minimize staining or discoloring of the gutta percha, the cannula 28 and housing 26 may be silver-plated.

Other embodiments of the cartridge 24 are contemplated. For example, the cannula 28 may be omitted from the cartridge 24 and coupled with another component of the obturator 22 (FIG. 2), such as the body 30 or heater 34.

Figure 3B:
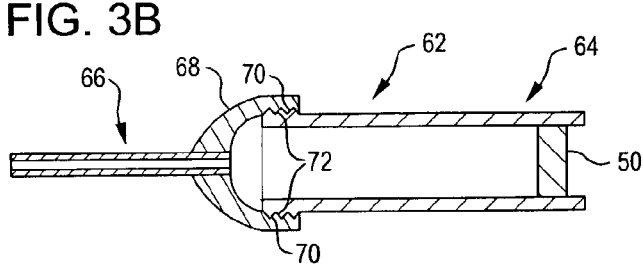
FIG. 3B is a cross-sectional view of a disposable cartridge according to another embodiment of the invention.

FIG. 3B is a cross-sectional view of a disposable cartridge 62 according to another embodiment of the invention. The cartridge 62 includes a housing 64 similar to the housing 26 in FIG. 3A, and a cannula 66 that may be removed from the housing 64 and replaced as desired. This may be desirable when a dentist or other medical technician wants to use two or more different cannulas during a procedure, such as a straight cannula to inject gutta percha into a front tooth of a patient and a curved cannula to inject gutta percha into a back tooth of the same patient.

The cannula 66 may be removably coupled with the housing 64 using any desired fastening technique. For example, in one embodiment, the cartridge 62 may include a cap 68 having internal threads 70, and the housing 64 may include external threads 72 that correspond with the internal threads 70. To couple the cannula 66 with the housing 64, the internal threads 70 are placed in contact with the external threads 72, and the cap 68 is rotated to slidingly engage the internal threads 70 with the external threads 72.

Figure 4:
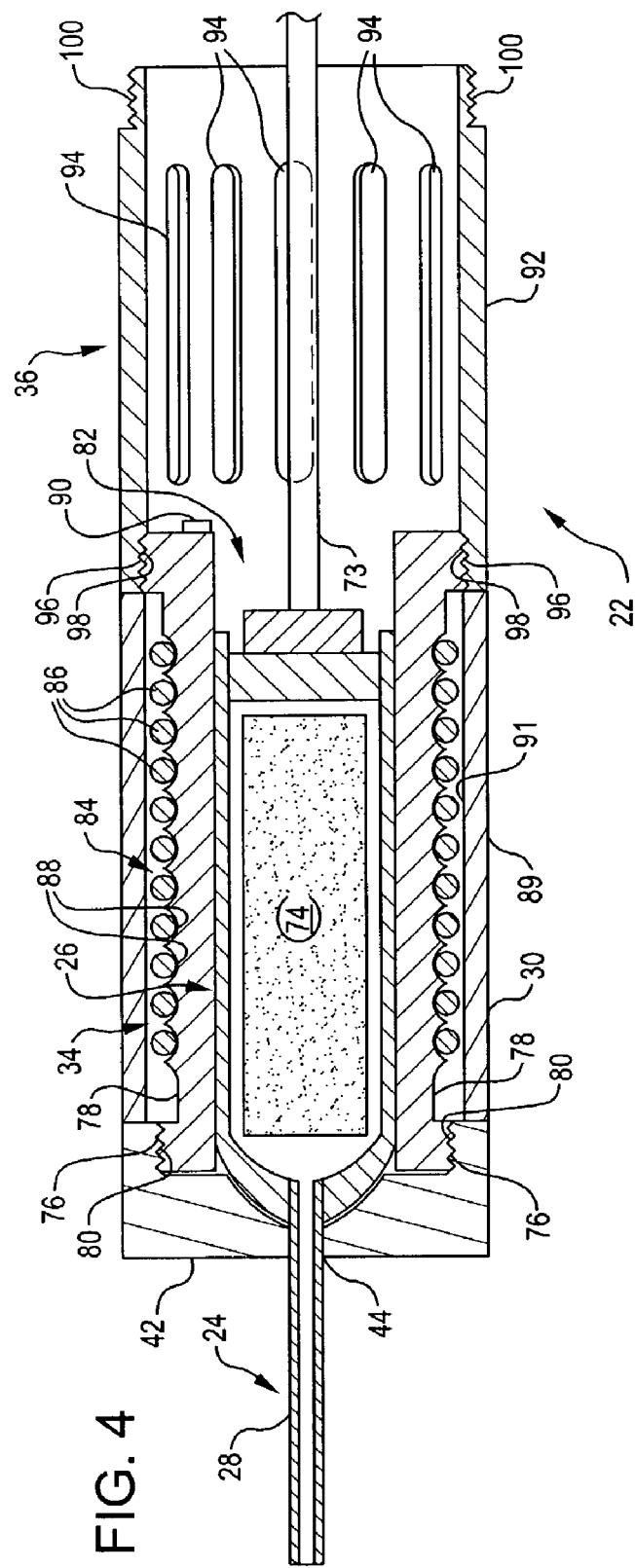
FIG. 4 is a cross-sectional view of a portion of the endodontic obturator in FIG. 2 showing the disposable cartridge coupled with a body of the obturator.

FIG. 4 is a cross-sectional view of a portion of the endodontic obturator 22 in FIG. 2, according to an embodiment of the invention, which shows the disposable cartridge 24 coupled with the body 30 of the obturator 22. Also shown in FIG. 4 is a component 73 of the mechanism 32 (FIG. 2 and discussed in greater detail in conjunction with FIG. 5) to generate pressure inside the housing 26 of the cartridge 24. The obturator 22 includes a heater 34 to raise the temperature of the gutta percha 74 contained in the cartridge 24 to soften and help dispense the gutta percha. The body 30 includes a thermal barrier 36 to resist the flow of heat from the heater 34 toward other components (not shown) and regions (not shown) of the obturator 22, such as the region a dentist or other medical technician typically uses to hold the obturator 22.

The cartridge 24 may be coupled with the body 30 of the obturator 22 using any desired fastening technique that secures the cartridge 24 with the body 30 while a dentist or other medical technician dispenses gutta percha from the cartridge 24, and that allows the dentist or other medical technician to quickly and easily couple/remove the cartridge 24 with/from the obturator 22 when desired. In one embodiment, the obturator 22 may include an attachment element 42 (also discussed in conjunction with FIG. 2) to removably couple the cartridge 24 with the body 30. The attachment element 42 may include internal threads 76, and the body 30 may include a receiver 78 having external threads 80 that correspond with the internal threads 76. The receiver 78 may also include a cartridge receptacle 82 sized to receive the housing 26 of the cartridge 24. To couple the cartridge 24 with the body 30, the dentist or other medical technician first inserts a portion or all of the housing 26 into the cartridge receptacle 82. Next, he/she inserts the cannula 28 of the cartridge 24 through the aperture 44 of the attachment element 42. Then, he/she rotates the attachment member 42 to slidingly engage the internal threads 76 with the external threads 80 of the receiver 78. Thus, the attachment element 42 couples the cartridge 24 with the body 30 by confining the housing 26 in the cartridge receptacle 82.

The heater 34 may generate heat using any desired technique and may be located near the cartridge receptacle 82 of the receiver 78 to efficiently raise the temperature of the gutta percha contained in the housing 26 when the cartridge 24 is coupled with the body 30. For example, in one embodiment, the heater 34 may include a coil 84 of one or more wires 86 and may generate heat by resisting the flow of electricity through the one or more wires 86. To keep electricity flowing through the whole coil 84, the receiver 78 may include grooves 88 that may be electrically insulated using conventional techniques, and the body 30 may include a heat shield 89, having an interior surface 91 that may also be electrically insulated using conventional techniques. In addition, the coil 84 may surround all or a portion of the receiver 26. Furthermore, the heater 34 may include control circuitry (not shown) to automatically stop or start the flow of electricity through the coil 84 when the temperature of the receiver 78 rises above or falls below a predetermined temperature. To monitor the temperature of the receiver 78, the heater 34 may include a conventional sensor 90. By monitoring, the temperature of the receiver 78, the control circuitry may obtain a close approximation of the temperature of the gutta percha 74. Thus, the heater 34 may be prevented from generating a substantially excessive amount of heat when heating the gutta percha 74. Consequently, the control circuitry may help reduce the temperature of a region of the obturator 22 where a dentist or medical technician holds the obturator.

Other embodiments of the heater 34 are contemplated. For example, the heater 34 may be a blanket that generates heat from electricity or the reaction of chemicals contained in the blanket.

Still referring to FIG. 4, the body 30 includes a thermal barrier 36 to resist the flow of heat from the heater 34 toward other components (not shown) and regions (not shown) of the obturator 22 such as a handle portion (shown in FIG. 5) of the body 30. In one embodiment, the thermal barrier 36 may include a cage 92 that receives heat from the heater 34 and transmits most of the heat to the air surrounding the cage 92. The cage 92 may include slots 94 to allow air to flow through the thermal barrier 36, and increase the surface area of the cage 92 exposed to the air surrounding the cage 92. Thus, a substantial portion of the heat received by the cage 92 may be transmitted to the air surrounding the cage 92. Furthermore, the cage 92 may be made from any desired material that is a poor conductor of heat, such as titanium.

Other embodiments of the thermal barrier 36 are contemplated. For example, the thermal barrier 36 may include vanes to increase the surface area exposed to the air surrounding the cage 92.

The thermal barrier 36 may be coupled with the receiver 78 and the remainder of the body 30 (discussed in greater detail in conjunction with FIG. 5) using any desired fastening technique. For example, in one embodiment, the cage 92 may include an internal thread 96 and the receiver 78 may include an external thread 98 that corresponds with the internal thread 96. To couple the cage 92 with the receiver 78, the receiver 92 is rotated to slidingly engage the external thread 98 with the internal thread 96 of the cage 92. Likewise, the cage 92 may include an external thread 100 that corresponds with an internal thread (not shown) of the remainder of the body 30.

Figure 5:
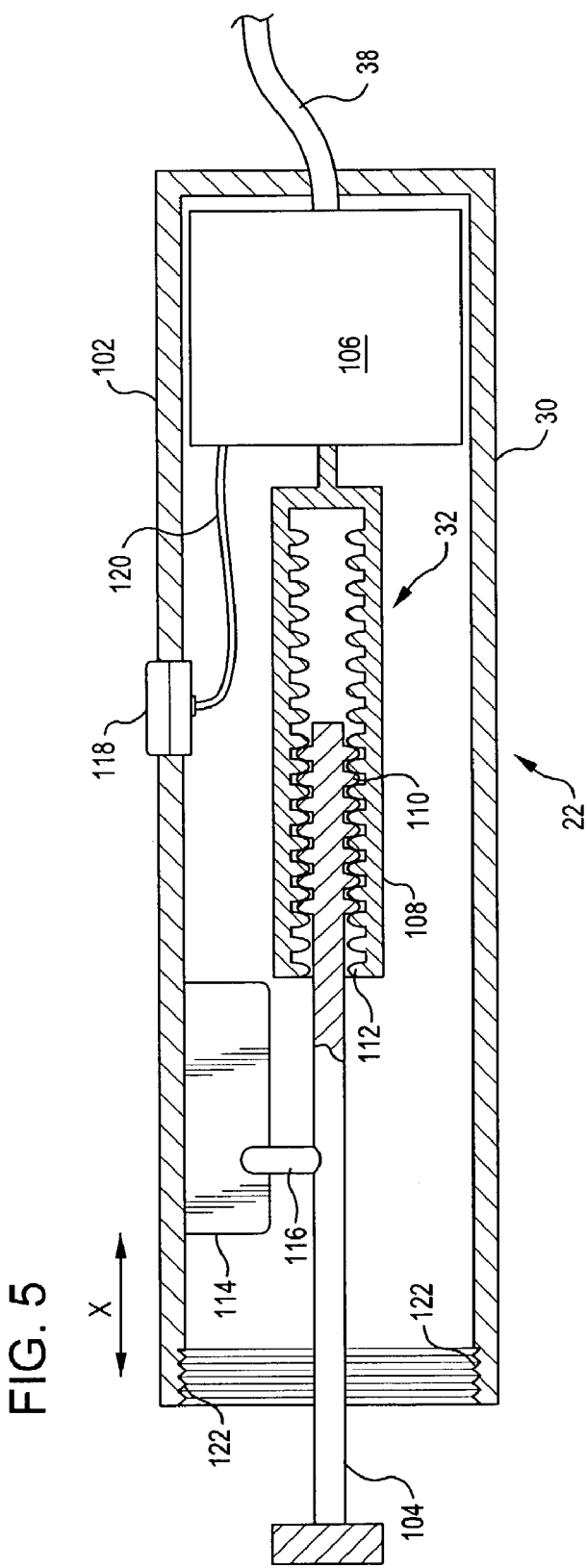
FIG. 5 is a cross-sectional view of the remaining portion of the endodontic obturator in FIG. 2 that includes a ram according to an embodiment of the invention.

FIG. 5 is a cross-sectional view of the remaining portion of the endodontic obturator 22 in FIG. 2, according to an embodiment of the invention. The obturator 22 includes a mechanism 32 to dispense the gutta percha 74 (FIG. 4) contained in the disposable cartridge 24 (FIG. 4). The body 30 of the obturator 22 includes a handle portion 102 that a dentist or other medical technician may use to hold onto the obturator 22 while he/she injects gutta percha into a patient's tooth.

In one embodiment, the mechanism 32 may include a ram 104 movable in the X direction toward the cartridge 24 to compress the gutta percha 74, a motor 106 to move the ram 104 in the X direction, and a screw 108 that couples the ram 104 with the motor 106. The motor 106 rotates the screw 108 to move the ram 104 in the X direction. The ram 104 may include an exterior thread 110 that slidingly engages an interior thread 112 of the screw 108 to couple the ram 104 with the screw 108. To move the ram 104 in the X direction, the interior thread 112 of the screw 108 should slide relative to the exterior thread 110 of the ram 104. However, when the motor 106 rotates the screw 108, the friction between the screw's interior thread 112 and the ram's exterior thread 110 cause the ram 104 to rotate also. So, to prevent the ram 104 from making a complete revolution, the body 30 may include a flange 114 that extends toward the ram 104, and the ram 104 may include a tab 116 that extends toward the body 30. Thus, when the screw 108 rotates, the ram 104 rotates until the tab 116 contacts the flange 114. Because the tab 116 prevents the screw 108 from further rotating the ram 104, the screw's interior thread 112 slides relative to the ram's exterior thread 110, which causes the ram 104 to move in the X direction. Thus, the screw 108 and the contact between the tab 116 and the flange 114 convert the motor's output shaft rotation into the ram's translation in the X direction.

Other embodiments of the mechanism 32 are contemplated. For example, the mechanism may include a ram that is moved by manually pivoting a lever connected to the ram.

Still referring to FIG. 5, the motor 106 may be any desired motor, such as an electric motor, and the mechanism 32 may further include a switch 118 to control the output of the motor 106 as desired. The switch 118 may be mounted to the body 30 and coupled with the motor 106 by a wire 120. In addition, the ram 104 and screw 108 may be made of any desirable material capable of withstanding wear in the external and internal threads 110 and 112, respectively, and stress generated by compressing the gutta percha 74 in the cartridge 24. For example, in one embodiment the ram 104 and screw 108 may be made of any conventional metal such as steel.

Still referring to FIG. 5, the handle 102 of the body 30 may be made of any desirable material and coupled with the thermal barrier 36 (FIG. 4) using any desired fastening technique. For example, in one embodiment, the handle 102 is made of conventional plastic and includes an internal thread 122 that corresponds with the thermal barrier's external thread 100 (FIG. 4). To couple the handle 102 of the body 30 with the cage 92 (FIG. 4) of the thermal barrier 36, the handle 102 is rotated to slidingly engage the internal thread 122 with the external thread 100 of the cage 92.

What is claimed is:

1. An endodontic obturator for dispensing gutta percha:
    a body having a handle portion for a dentist or other medical technician to hold while dispensing gutta percha;
    a disposable cartridge coupleable with the body and containing the gutta percha to be dispensed;
    a mechanism operable to generate pressure in the disposable cartridge to dispense the gutta percha from the cartridge;
    a heater operable to heat the gutta percha in the cartridge to help dispense the gutta percha from the cartridge; and
    a thermal barrier that separates the heater from the handle portion of the body, and is operable to resist the flow of heat from the heater to the handle portion.

2. The obturator of claim 1 further comprising an attachment element operable to couple the disposable cartridge with the body.

3. The obturator of claim 1 wherein the disposable cartridge is removable from the body and replaceable.

4. The obturator of claim 1 wherein the body includes a receiver having a cartridge receptacle operable to receive the disposable cartridge.

5. The obturator of claim 1 wherein the disposable cartridge includes:
    a housing defining a chamber operable to hold gutta percha, and
    a cannula coupled with the body and including a conduit in fluid communication with the chamber, wherein the gutta percha flows through the conduit when the gutta percha is dispensed from the cartridge.

6. The obturator of claim 1 wherein the mechanism includes a ram movable relative to the disposable cartridge to generate pressure in the cartridge.

7. The obturator of claim 6 wherein the mechanism includes a motor operable to move the ram relative to the disposable cartridge to generate pressure in the cartridge.

8. The obturator of claim 7 wherein the motor is an electric motor.

9. The obturator of claim 1 wherein the heater includes a coil of wire operable to generate heat by resisting the flow of electricity through the wire.

10. The obturator of claim 1 wherein:
    the body includes a receiver having a cartridge receptacle operable to receive the disposable cartridge, and
    the heater surrounds a portion of the receiver.

11. The obturator of claim 1 wherein:
    the body includes a receiver having a cartridge receptacle operable to receive the disposable cartridge, and
    the heater is operable to monitor the temperature of the receiver and stop or start generating heat according to the temperature of the receiver.

12. A method comprising:
    coupling a disposable cartridge containing gutta percha to an obturator operable to dispense gutta percha from the cartridge;
    heating the gutta percha with a heater of the obturator;
    dispensing the gutta percha from the cartridge; and
    resisting, with a thermal barrier disposed between the heater and a portion of the obturator that does not surround the cartridge, the flow of heat from the heater toward the handle portion.

13. The method of claim 12 wherein coupling the disposable cartridge containing gutta percha includes inserting a housing of the disposable cartridge into a cartridge receptacle of the obturator.

14. The method of claim 12 wherein coupling the disposable cartridge containing gutta percha includes;
   inserting a housing of the disposable cartridge into a cartridge receptacle of a receiver of the obturator, and threading an attachment element with the receiver to confine the housing in the cartridge receptacle.

15. The method of claim 12 wherein dispensing the gutta percha from the disposable cartridge includes moving a ram of the obturator toward the cartridge to generate pressure in the cartridge.

16. The method of claim 15 wherein moving the ram includes rotating an output shaft of a motor.

17. The method of claim 12 wherein dispensing the gutta percha from the disposable cartridge includes moving the gutta percha through a cannula of the disposable cartridge.

18. The method of claim 12 further comprising removing the disposable cartridge from the obturator.

19. An endodontic obturator for dispensing gutta percha:
   a body having a handle portion for a dentist or other medical technician to hold while dispensing gutta percha;
   a disposable cartridge coupleable with the body and containing the gutta percha to be dispensed;
   a mechanism operable to generate pressure in the disposable cartridge to dispense the gutta percha from the cartridge;
   a heater operable to heat the gutta percha in the cartridge to help dispense the gutta percha from the cartridge; and
   a thermal barrier that separates the heater from the handle portion of the body and is operable to remove heat from the obturator.

20. A method comprising:
   coupling a disposable cartridge containing gutta percha to an obturator operable to dispense gutta percha from the cartridge;
   heating the gutta percha;
   dispensing the gutta percha from the cartridge;
   separating, with a thermal barrier, a heater of the obturator from a handle portion of the obturator; and
   removing heat from the obturator.

* * * * *